(12) United States Patent
Hoshino

(10) Patent No.: US 8,801,604 B2
(45) Date of Patent: Aug. 12, 2014

(54) ELECTRONIC ENDOSCOPE WITH LAMINATED TUBE MEMBER

(75) Inventor: Yuki Hoshino, Atsugi (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/525,518

(22) Filed: Jun. 18, 2012

(65) Prior Publication Data
US 2012/0271108 A1    Oct. 25, 2012

Related U.S. Application Data

(63) Continuation of application No. PCT/JP2010/070305, filed on Nov. 15, 2010.

(30) Foreign Application Priority Data

Jan. 25, 2010    (JP) ................................ 2010-013393

(51) Int. Cl.
*A61B 1/00*      (2006.01)
*A61B 1/005*      (2006.01)
*A61B 1/12*      (2006.01)
*G02B 23/24*      (2006.01)
*H01R 9/03*      (2006.01)

(52) U.S. Cl.
CPC .......... *A61B 1/00009* (2013.01); *A61B 1/00114* (2013.01); *A61B 1/00018* (2013.01); *A61B 1/00091* (2013.01); *A61B 1/0011* (2013.01); *A61B 1/00119* (2013.01); *A61B 1/00124* (2013.01); *A61B 1/0055* (2013.01); *A61B 1/126* (2013.01); *G02B 23/2476* (2013.01); *H01R 9/037* (2013.01)
USPC .............. 600/132; 600/140; 174/78; 439/578

(58) Field of Classification Search
USPC .......... 600/132, 139, 140, 134; 174/78, 74 R; 439/578, 584, 585
See application file for complete search history.

(56) References Cited

U.S. PATENT DOCUMENTS 3,739,076 A * 6/1973 Schwartz ........................ 174/78
3,744,007 A * 7/1973 Horak ............................ 439/394

(Continued)

FOREIGN PATENT DOCUMENTS

CN    101587239 A    11/2009
EP    2 123 209    11/2009

(Continued)

OTHER PUBLICATIONS

Translation of Jp 2008-32801, Feb. 14, 2008.*

(Continued)

*Primary Examiner* — John P Leubecker
(74) *Attorney, Agent, or Firm* — Scully, Scott, Murphy & Presser, P.C.

(57) ABSTRACT

A flexible tube portion of an insertion portion of an electronic endoscope and a universal cable each includes a laminated tube member and a corrugated tube connection member. The laminated tube member includes a conductive tube member and an insulating cover covering the conductive tube member. The corrugated tube connection member includes a fixing hole where an end portion of the laminated tube member is inserted. The end portion of the laminated tube member is adhesively fixed. The end portion of the laminated tube member is an electrical connection portion, and the conductive tube member is exposed. The corrugated tube connection member includes a conductive elastic member in the fixing hole. The conductive elastic member electrically connects the electrical connection portion to the corrugated tube connection member. The conductive elastic member is elastically deformable radially and contacts an outer surface of the conductive tube member with a predetermined pressing force.

5 Claims, 18 Drawing Sheets

(56) References Cited

U.S. PATENT DOCUMENTS

| | | | | |
|---|---|---|---|---|
| 3,830,957 | A | * | 8/1974 | Oberdiear ............... 174/78 |
| 4,022,966 | A | * | 5/1977 | Gajajiva ............... 174/653 |
| 4,540,231 | A | * | 9/1985 | Forney, Jr. ............... 439/306 |
| 4,598,165 | A | * | 7/1986 | Tsai ............... 174/36 |
| 5,059,747 | A | * | 10/1991 | Bawa et al. ............... 174/655 |
| 5,469,841 | A | | 11/1995 | Kobayashi et al. |
| 5,746,696 | A | * | 5/1998 | Kondo ............... 600/139 |
| 5,873,816 | A | * | 2/1999 | Kagawa et al. ............... 600/134 |
| 5,876,326 | A | * | 3/1999 | Takamura et al. ............... 600/110 |
| 5,942,730 | A | * | 8/1999 | Schwarz et al. ............... 174/84 R |
| 5,993,253 | A | * | 11/1999 | Sai ............... 439/578 |
| 6,019,615 | A | * | 2/2000 | Masuda ............... 439/99 |
| 6,809,265 | B1 | * | 10/2004 | Gladd et al. ............... 174/74 R |
| 7,097,499 | B1 | * | 8/2006 | Purdy ............... 439/578 |
| 2009/0171158 | A1 | * | 7/2009 | Matsuo et al. ............... 600/139 |
| 2009/0292169 | A1 | * | 11/2009 | Mitani et al. ............... 600/110 |

FOREIGN PATENT DOCUMENTS

| | | |
|---|---|---|
| JP | 2001-258825 | 9/2001 |
| JP | 2008-032801 | 2/2008 |

OTHER PUBLICATIONS

International Search Report dated Dec. 7, 2010 issued in PCT/JP2010/070305.

European Search Report dated Nov. 15, 2012 from corresponding European Patent Application No. EP 10 84 3941.5.

Chinese Office Action dated Feb. 8, 2014 in corresponding Chinese Patent Application No. 201080054464.0.

* cited by examiner

Prior Art  FIG.1
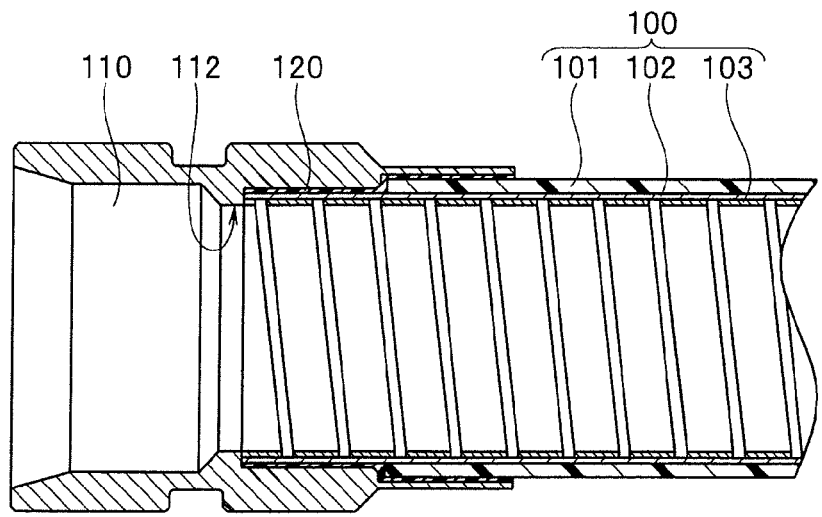
Prior Art  FIG.2
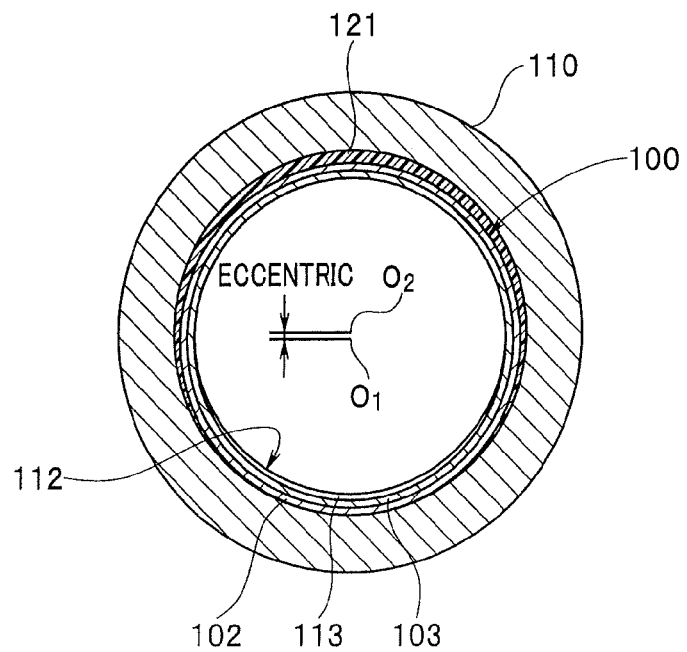

ELECTRONIC ENDOSCOPE WITH LAMINATED TUBE MEMBER

CROSS REFERENCE TO RELATED APPLICATION

This application is a continuation application of PCT/JP2010/070305 filed on Nov. 15, 2010 and claims benefit of Japanese Application No. 2010-013393 filed in Japan on Jan. 25, 2010, the entire contents of which are incorporated herein by this reference.

BACKGROUND OF THE INVENTION

1. Field of the Invention

The present invention relates to an electronic endoscope that reduces radiation of extraneous emission noises.

2. Description of the Related Art

In recent years, for endoscope apparatuses including devices such as video processors that incorporate electronic circuits configuring image processing units or the like, there has been increasing need for measures against EMC (a generic term for EMI, a problem of giving electromagnetic interference, and EMS, a problem of receiving electromagnetic interference). In particular, in a field of medical equipment used in hospitals, EMC measures are necessary.

In an endoscope that inserts an elongated insertion portion into a body to observe an affected area or the like in the body, for example, a solid image pickup device such as a CCD is incorporated in a distal end portion of the insertion portion. An electrical signal photoelectrically converted by a solid image pickup device is transmitted to a video processor through a signal cable inserted in the insertion portion, an operation portion, and a universal cable. The video processor converts the transmitted electrical signal into a video signal and then outputs the video signal to a monitor apparatus.

Flexible tube portions of insertion portions and universal cables that configure endoscopes have flexibility. As shown in FIG. 1, a flexible tube portion and a universal cable are mainly composed of a laminated tube member (hereinafter, referred to as a corrugated tube) 100 configured by laminating a cover 101, a mesh-tube 102, and a helical tube 103. The cover 101 is insulating resin. The mesh-tube 102 is conductive tubular wire mesh and positioned inside the cover 101. The helical tube 103 is obtained by winding a strip-shaped conductive member into a spiral shape and positioned inside the mesh-tube 102.

In a conventional endoscope, at both ends of the corrugated tube 100, the cover 101 is scraped off so as to expose the mesh-tube 102. Then, the exposed mesh-tube 102 is electrically connected to a conductive corrugated tube connection member 110 so as to be electrically conductive with a metal member forming a sheath of the endoscope. Thereby, an unwanted current flowing through the sheath and causing an extraneous emission noise is fallen to the ground and an electromagnetic wave shielding property is established.

In order to achieve an inexpensive and small endoscope, the corrugated tube connection member 110 and the mesh-tube 102 may be adhesively secured to each other. However, if an adhesive for adhesively securing enters a gap between an inner circumferential face of the corrugated tube connection member 110 and an outer circumferential face of the mesh-tube 102 to form an adhesive layer 120, there arises a problem that electrical conductivity is impaired.

To solve the problem, as shown in FIG. 2, an adhesion portion 121 has been provided with a center O1 of the corrugated tube 100 being eccentric with respect to a center O2 of the corrugated tube connection member 110 and a part of the outer circumferential face of the mesh-tube 102 being in contact with the inner circumferential surface of the corrugated tube connection member 110, and the corrugated tube 100 and the corrugated tube connection member 110 have been adhesively secured to each other.

Also, in an endoscope apparatus disclosed in Japanese Patent Application Laid-Open Publication No. 2008-32801, a sixth embodiment indicates a thin-plate-shaped ring member in which a plurality of leaf spring pieces are provided and spaced apart from each other at regular distances. In the endoscope apparatus, a snap ring is screwed with a rear-end mouth ring and the leaf spring pieces are deformed radially inward as the snap ring rotates. Thereby, inside faces of the leaf spring pieces are brought into contact with an outer surface of a short tube to cause the short tube and the rear-end mouth ring to be conductive with each other.

SUMMARY OF THE INVENTION

An electronic endoscope of an aspect of the present invention is an electronic endoscope including: a laminated tube member having conductive tube members configuring a flexible tube portion of an insertion portion and a universal cable, and an insulating cover covering the conductive tube members; and a conductive corrugated tube connection member having a fixing hole in which an end portion of the laminated tube member is inserted, in which the end portion of the laminated tube member inserted in the fixing hole is adhesively secured, wherein the laminated tube member installed in the fixing hole includes, at the end portion of the laminated tube member, an electrical connection portion being a conductive tube member exposed by peeling the insulating cover, and the corrugated tube connection member includes, in the fixing hole, a conductive elastic member that is elastically deformable radially, electrically connects the electrical connection portion to the corrugated tube connection member, and has an urging force for contacting an outer surface of the conductive tube member with a predetermined pressing force.

BRIEF DESCRIPTION OF THE DRAWINGS

FIG. 1 is a diagram illustrating a configuration of a laminated tube member and illustrating an adhesive layer formed between an inner circumferential face of a connection tube and an outer circumferential face of a mesh-tube in accordance with an example of a configuration of a conventional electronic endoscope;

FIG. 2 is a diagram illustrating adhesive securing between a laminated tube member and a connection tube by pushing a part of an outer circumferential face of a mesh-tube against an inner circumferential face of the connection tube to provide an adhesion portion in accordance with an example of a configuration of a conventional electronic endoscope;

DETAILED DESCRIPTION OF THE PREFERRED EMBODIMENT

Embodiments of the present invention will now be described in detail with reference to the drawings.

The embodiments of the present invention will now be described with reference to the drawings.

An embodiment of the present invention will be described with reference to FIG. 3 through FIG. 19.

Figure 3:
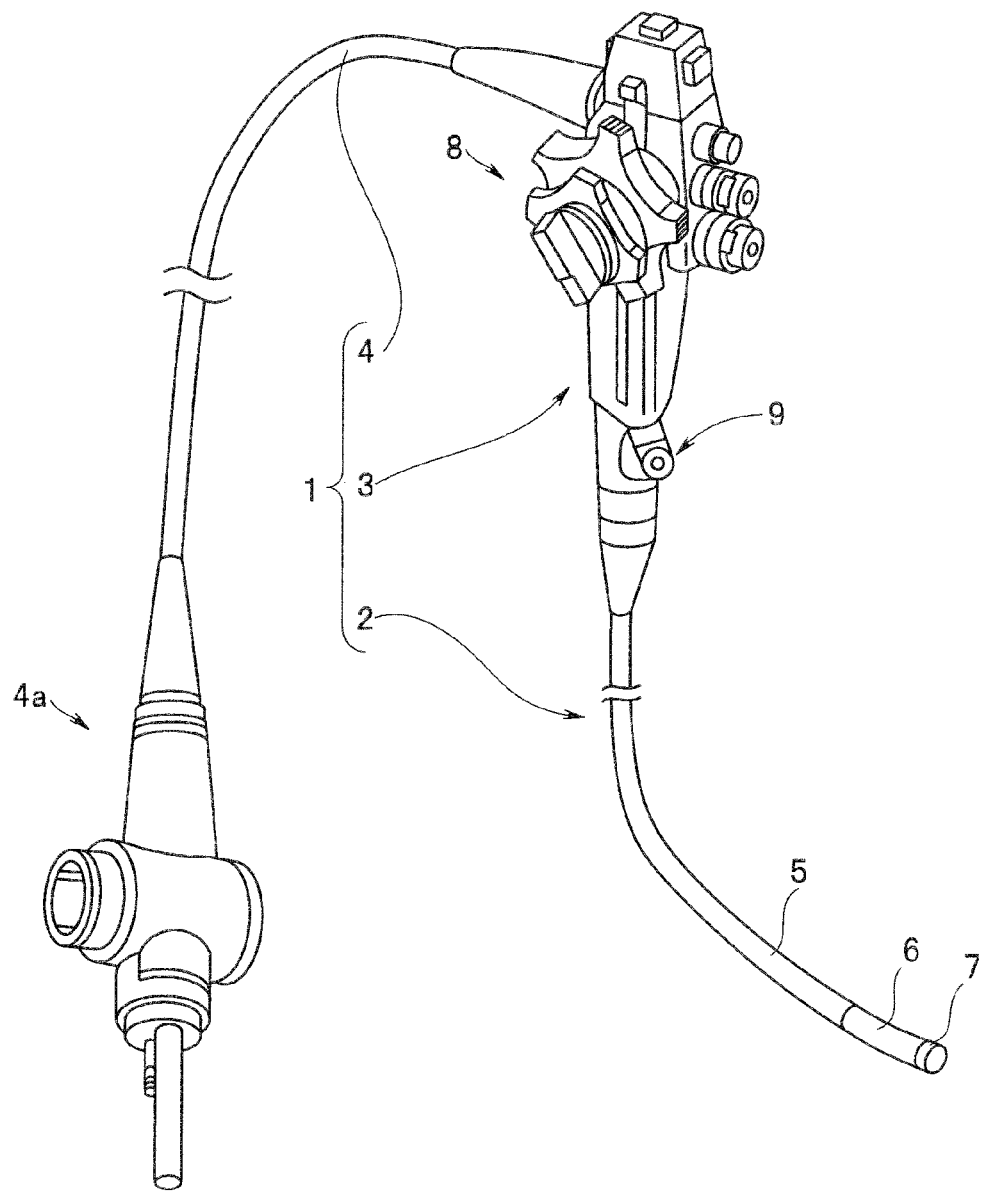
FIG. 3 is a diagram illustrating a configuration of an electronic endoscope according to an embodiment of the present invention.

As shown in FIG. 3, an electronic endoscope 1 mainly includes an elongated insertion portion 2 to be inserted into a body, an operation portion 3 provided at a proximal end of the insertion portion 2, and a universal cable 4 extending from a side of the operation portion 3. A connector 4a is provided at an end portion of the universal cable 4. The connector 4a is detachably connected with a light source apparatus and a video processor, not shown.

The insertion portion 2 includes an elongated flexible tube portion 5 with flexibility, a bendable bending portion 6 connected to a distal end of the flexible tube portion 5, and a rigid distal end portion 7 connected to a distal end of the bending portion 6.

The operation portion 3 is provided with a bending operation knob 8 and a treatment instrument insertion opening 9. An operator can rotate the bending operation knob 8 to bend the bending portion 6 in a desired direction. Also, the operator can lead a treatment instrument from the treatment instrument insertion opening 9 and a treatment instrument channel (see reference numeral 74 in FIG. 20 described later) into a body to treat an affected area or the like via a distal end opening, not shown, of the distal end portion 7.

The flexible tube portion 5 of the insertion portion 2 and the universal cable 4 each have corrugated tube configurations with flexibility.

Figure 4:
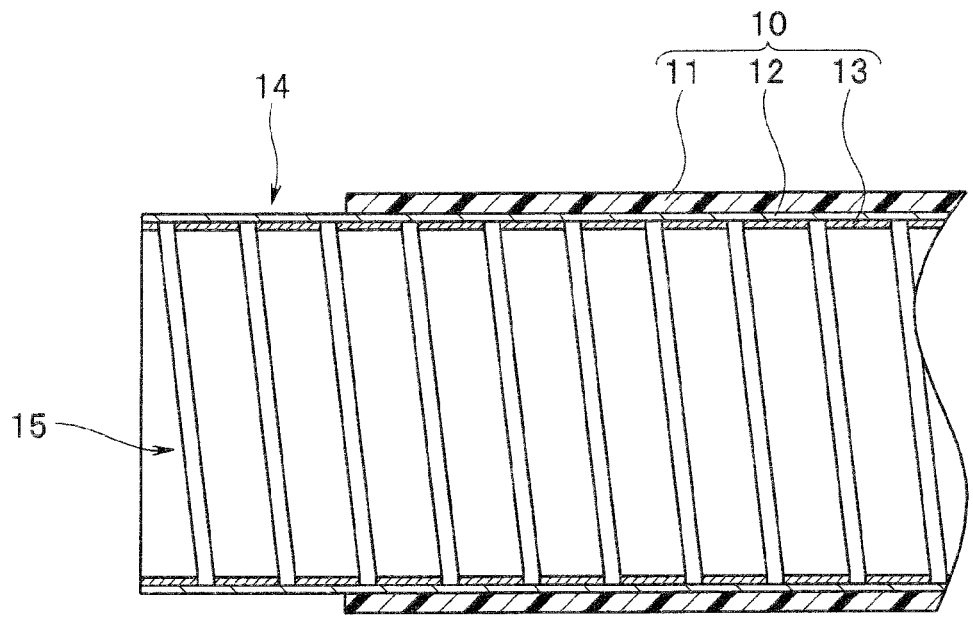
FIG. 4 is a cross-sectional view illustrating a lamination structure of a corrugated tube.

Reference numeral 10 in FIG. 4 denotes a corrugated tube which configures the universal cable 4, for example. A corrugated tube 10 is a laminated tube member formed by laminating a cover 11, a mesh-tube 12, and a helical tube 13, and has a through hole 15 from a distal end to a proximal end.

The helical tube 13 is obtained by winding a strip-shaped conductive metal thin plate into a spiral shape. The mesh-tube 12 is a conductive tubular wire mesh formed by twisting a conductive metal thin line into a braided configuration. The mesh-tube 12 wraps the helical tube 13. The helical tube 13 and the mesh-tube 12 configure a conductive tube member. The cover 11 is a flexible and insulating resin member. The cover 11 covers the mesh-tube 12.

In the present embodiment, both ends of the corrugated tube 10 are provided with electrical connection portions 14. Only one end side is shown in FIG. 4, and the other end side, not shown, has a configuration similar to that of the foregoing one end side. The electrical connection portion 14 is an exposed part of the mesh-tube 12 obtained by peeling the cover 11 off an end face of the conductive tube member by a predetermined dimension.

It should be noted that a corrugated tube that configures the flexible tube portion 5 and is not shown may have an outside diameter, a length, or other dimensions different from those of the corrugated tube 10, but since a main configuration is substantially the same as the corrugated tube 10, a description thereof is omitted.

Figure 5:
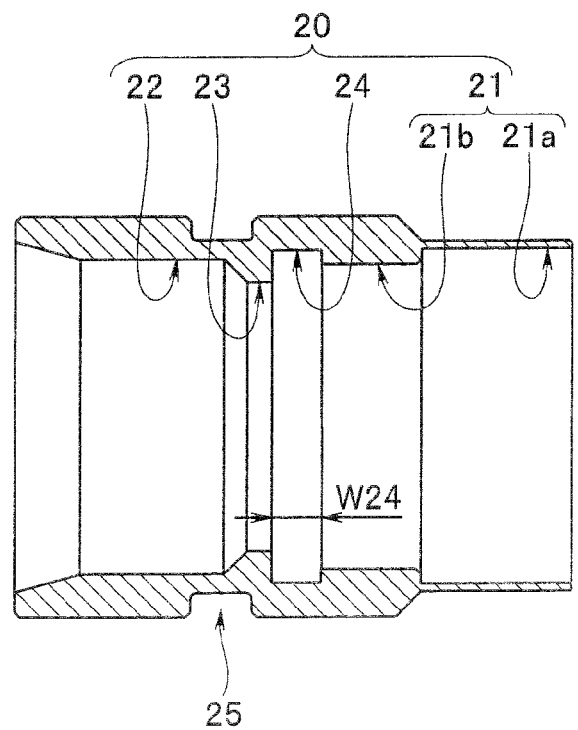
FIG. 5 is a cross-sectional view illustrating a configuration of a connector-side corrugated tube connection member.

Reference numeral 20 in FIG. 5 denotes a connector-side corrugated tube connection member. The connector-side corrugated tube connection member 20 is provided at a side of the connector 4a of the universal cable 4. The connector-side corrugated tube connection member 20 is, for example, a conductive metal pipe-shaped member. The connector-side corrugated tube connection member 20 includes a fixing connection hole 21, a connecting hole 22, a communicating hole 23, and a circumferential concave portion 24. The fixing connection hole 21 is a fixing hole. The fixing connection hole 21 is a stepped hole having a thick hole and a thin hole concentric with each other. The thick hole is positioned at the side of the end face. The thick hole is a cover installation hole 21a and the cover 11 of the corrugated tube 10 is installed therein. An inside diameter dimension of the cover installation hole 21a is larger than an outside diameter dimension of the cover 11 by a predetermined dimension. Thus, when the cover 11 is installed in the cover installation hole 21a, a gap in which adhesive is filled is formed between the inner face of the cover installation hole 21a and the outer face of the cover 11.

The thin hole of the fixing connection hole 21 is a mesh-tube installation hole 21b and the mesh-tube 12 of the corrugated tube 10 is installed. An inside diameter dimension of the mesh-tube installation hole 21b is larger than an outside diameter dimension of the mesh-tube 12 by a predetermined dimension. Thus, when the mesh-tube 12 is installed in the mesh-tube installation hole 21b, a gap in which adhesive is filled is formed between the inner face of the mesh-tube installation hole 21b and the outer face of the mesh-tube 12.

The circumferential concave portion 24 is formed on the inner face of the mesh-tube installation hole 21b, for example, at a base side.

In the connecting hole 22, a signal cable, an air feed tube, a water feed tube, and a sucking tube, which are not shown, are inserted.

The communicating hole 23 communicates the mesh-tube installation hole 21b with the connecting hole 22.

An inside diameter dimension of the communicating hole 23 and an inside diameter dimension of the through hole 15 of the corrugated tube 10 are configured to be substantially the same. In the communicating hole 23 and the through hole 15, the signal cable, the air feed tube, the water feed tube, and the sucking tube, inserted in the connecting hole 22, are inserted.

The circumferential concave portion 24 is a conductive member installation portion. The circumferential concave portion 24 is formed as a circumferential groove of a predetermined depth dimension from the inner face of the mesh-tube installation hole 21b. In the circumferential concave portion 24, a first spring portion 31 of a conductive elastic member described later (see reference numeral 30 in FIG. 6 and the like) is installed.

Reference numeral 25 denotes a circumferential groove for O-ring, and an O-ring, not shown, is installed therein. The circumferential groove for O-ring 25 is formed on the outer circumferential face of the connector-side corrugated tube connection member 20.

Also, at a side of the operation portion 3 of the universal cable 4, an operation portion side corrugated tube connection member, not shown, is provided. An outside diameter dimension, a length dimension, and the like of the operation portion side corrugated tube connection member may be different from those of the connector-side corrugated tube connection member 20, but because a main configuration is substantially the same as that of the connector-side corrugated tube connection member 20, a description thereof is omitted.

The conductive elastic member 30 is a metal member that is elastically deformable and conductive. For example, the conductive elastic member 30 is formed of a plate member such as a phosphor bronze plate.

Figure 6:
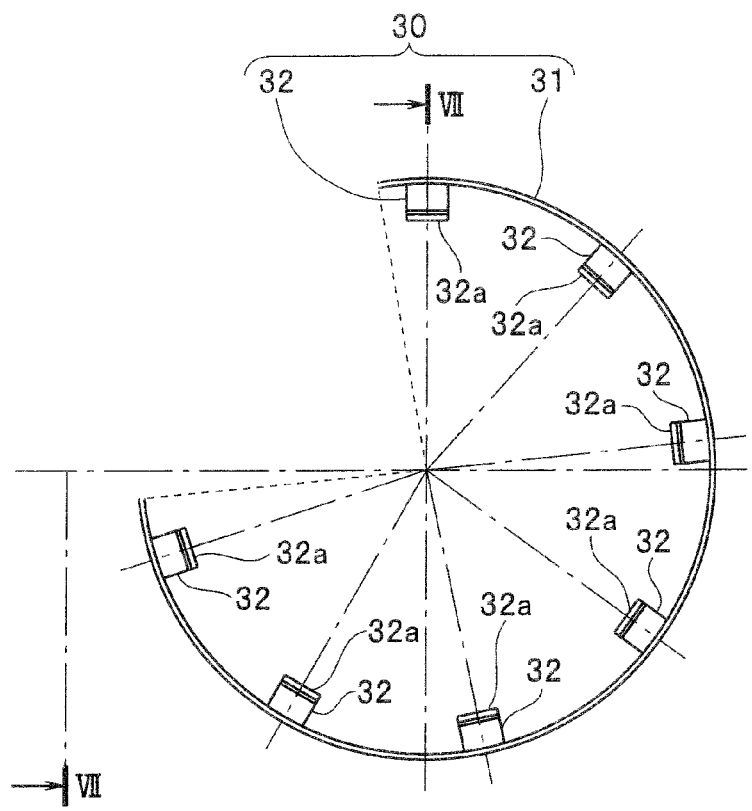
FIG. 6 is a diagram illustrating an example of a configuration of a conductive elastic member.
Figure 7:
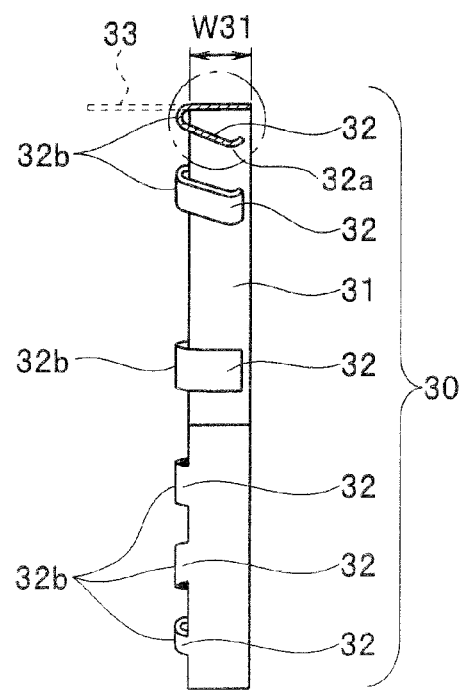
FIG. 7 is a cross-sectional view taken along a line VII-VII in FIG. 6.

As shown in FIGS. 6 and 7, the conductive elastic member 30 includes the first spring portion 31 and second spring portions 32.

The first spring portion 31 is substantially C-shaped with a cutout and elastically deformable radially. A width dimension W31 of a plate member forming the first spring portion 31 is smaller than a width dimension W24 of the circumferential concave portion 24 by a predetermined dimension. Thus, the first spring portion 31 can be installed in the circumferential concave portion 24 and is prevented from moving in a longitudinal axis direction of the connector-side corrugated tube connection member 20.

The plurality of second spring portions 32 are circumferentially provided on the first spring portion 31 at predetermined regular intervals. The second spring portions 32 are obtained by bending a plurality of convex strips 33 provided on the first spring portion 31 and indicated by dashed lines. Contact faces 32a of the second spring portions 32 are oriented to the center of the first spring portion 31. That is, the second spring portions 32 are formed so as to have urging force to a center axis direction of the corrugated tube 10. Then, the contact faces 32a are installed on the outer surface of the mesh-tube 12, and thereby each of the contact faces 32a presses the outer surface of the mesh-tube 12 with a predetermined pressing force.

In the foregoing, the corrugated tube connection member is a metal pipe-shaped member having conductivity and the circumference. However, a cross-sectional shape of the pipe-shaped member is not limited to a circle and may be a polygonal. If polygonal, an equilateral polygon such as a square and an equilateral hexagon is desirable.

A configuration of the universal cable 4 and a procedure for assembling the universal cable 4 will be described with reference to FIGS. 8 to 10C.

Figure 8:
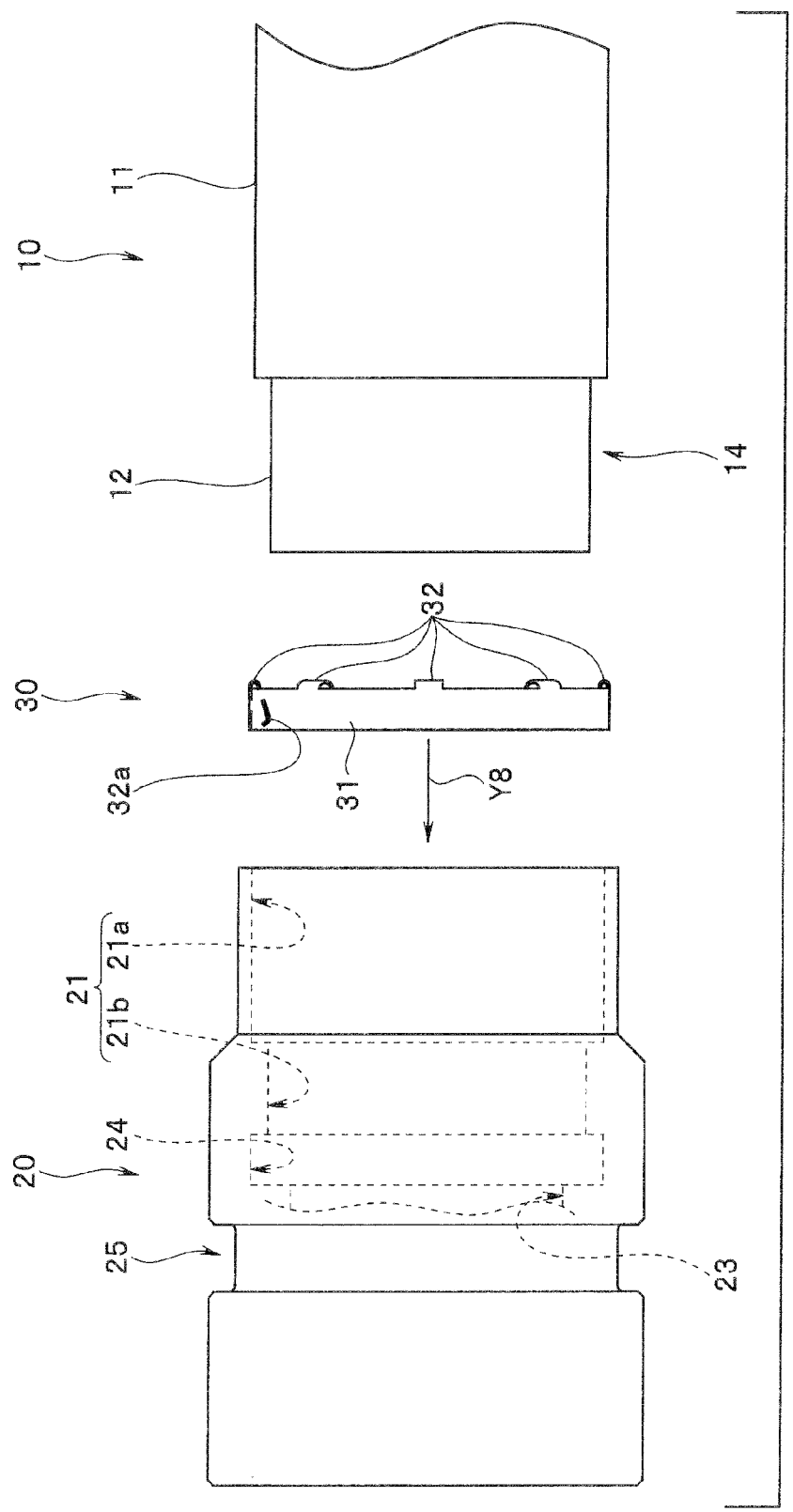
FIG. 8 is a diagram illustrating a procedure for installing a conductive elastic member in a circumferential concave portion of a connector-side corrugated tube connection member in accordance with a procedure for assembling a universal cable.

The universal cable 4 is composed of the corrugated tube 10, the connector-side corrugated tube connection member 20, and the two conductive elastic members 30, which are shown in FIG. 8, and an operation portion side corrugated tube connection member, not shown.

The procedure for assembling the universal cable 4 will now be described.

The operator prepares the corrugated tube 10, the connector-side corrugated tube connection member 20, and the conductive elastic members 30.

First, the operator installs the conductive elastic member 30 in the circumferential concave portion 24 of the connector-side corrugated tube connection member 20. At this time, the operator orients the second spring portions 32 of the conductive elastic member 30 to predetermined directions to make the first spring portion 31 narrow against the urging force of the first spring portion 31.

Next, the operator moves the narrowed first spring portion 31 in an axis direction as indicated by an arrow Y8 and inserts the first spring portion 31 in the cover installation hole 21a through an end face opening. The operator then leads the narrowed first spring portion 31 into the circumferential concave portion 24 through the cover installation hole 21a and the mesh-tube installation hole 21b.

Figure 9:
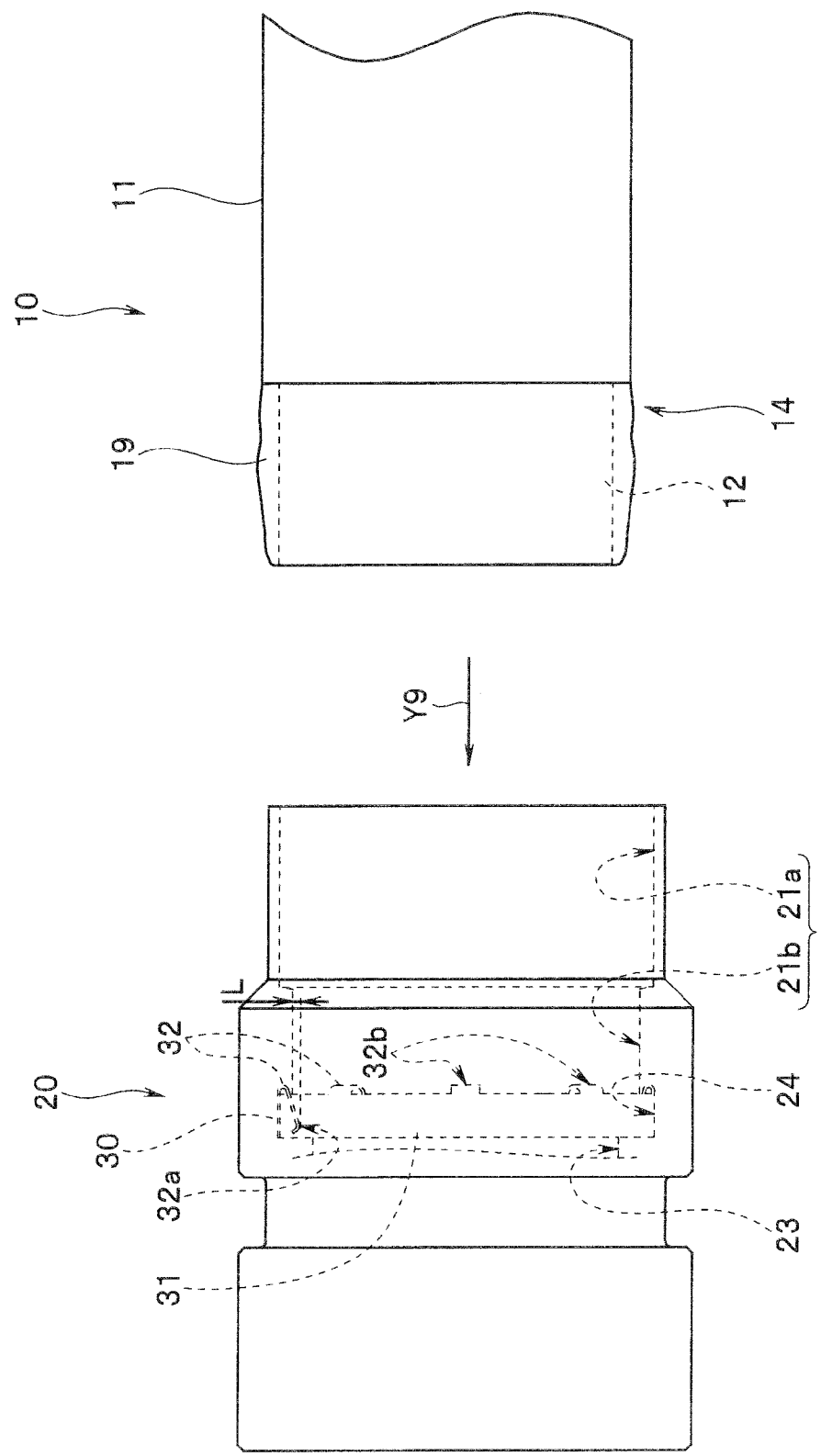
FIG. 9 is a diagram illustrating a procedure for inserting a corrugated tube with an adhesive applied on an electrical connection portion toward the conductive elastic member installed in the circumferential concave portion in accordance with the procedure for assembling the universal cable.

Then, as shown in FIG. 9, the first spring portion 31 is changed from the narrow state to an opened state by the urging force. At this time, the outer circumferential face of the first spring portion 31 is brought into intimate contact with the inner circumferential face of the circumferential concave portion 24 by the urging force. Therefore, the conductive elastic member 30 is electrically connected to the connector-side corrugated tube connection member 20.

In the installation state, the contact faces 32a of the second spring portions 32 are installed in the mesh-tube installation hole 21b and protrude from the inner face of the mesh-tube installation hole 21b to the center axis direction of the connector-side corrugated tube connection member 20 by a predetermined dimension L as shown in FIG. 9.

Next, the operator applies an adhesive 19 onto the outer surface of the electrical connection portion 14 of the corrugated tube 10. Thereafter, the operator moves the electrical connection portion 14 onto which the adhesive 19 has been applied in the axis direction as indicated by an arrow Y9 and inserts the electrical connection portion 14 in the cover installation hole 21a through the end face opening. Then, the operator moves the corrugated tube 10 in the axis direction to cause the electrical connection portion 14 to approach the contact faces 32a in the mesh-tube installation hole 21b.

The electrical connection portion 14 onto which the adhesive 19 has been applied moves in the axis direction through the cover installation hole 21a and the mesh-tube installation hole 21b. Then, the applied adhesive 19 enters a gap between the inner face of the cover installation hole 21a and the outer face of the cover 11, and a gap between the inner face of the mesh-tube installation hole 21b and the outer face of the mesh-tube 12.

Figure 10A:
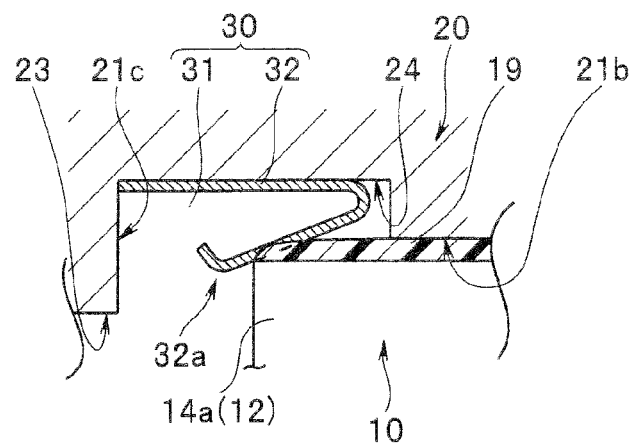
FIG. 10A is a diagram illustrating a state in which an end face of the corrugated tube inserted in the electrical connection portion abuts a second spring portion in accordance with the procedure for assembling the universal cable.

Then, as shown in FIG. 10A, the distal end face of the corrugated tube 10 abuts the second spring portions 32. As a result, the movement of the corrugated tube 10 in the axis direction stops.

Figure 10B:
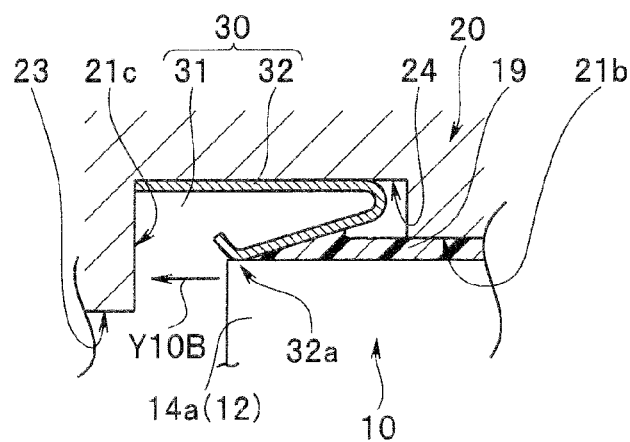
FIG. 10B is a diagram illustrating a state in which a contact face of the second spring portion is installed on a mesh-tube being an outer surface at an end face side of the electrical connection portion in accordance with the procedure for assembling the universal cable.

Now, the operator further moves the corrugated tube 10 toward a base 21c of the mesh-tube installation hole 21b against the urging force of the plurality of the second spring portions 32. As a result, as shown in FIG. 10B, the contact faces 32a are installed on an end face side outer surface of the electrical connection portion 14, namely, on the mesh-tube 12. At this time, because the contact faces 32a are pressing the outer surface of the mesh-tube 12 with a predetermined urging force, the contact faces 32a are directly in contact with the mesh-tube 12 with the adhesive 19 that has been applied on the electrical connection portion 14 being removed.

Now, the operator further moves the corrugated tube 10 toward the base 21c in the axis direction as indicated by an arrow Y10B in the figure. As a result, while removing the adhesive 19 applied on the electrical connection portion 14, the contact faces 32a move along the mesh-tube 12 without leaving the outer surface of the mesh-tube 12. That is, the adhesive 19 applied on the electrical connection portion 14 is removed as the plurality of contact faces 32a pressing the outer surface of the mesh-tube 12 move in the axis direction.

Figure 10C:
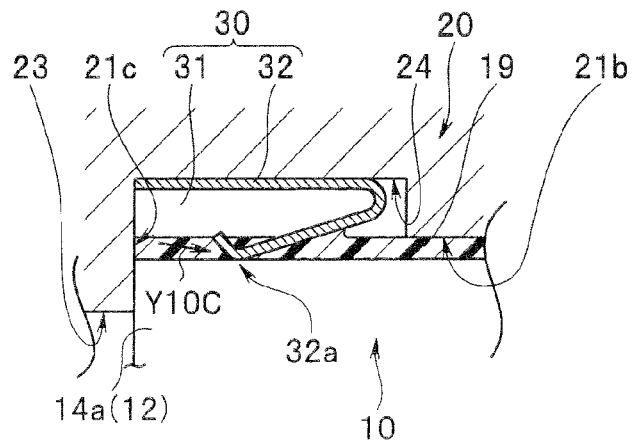
FIG. 10C is a diagram illustrating a state in which the corrugated tube is inserted in a connector-side corrugated tube connection member and installed in a predetermined condition in accordance with the procedure for assembling the universal cable.

Then, the corrugated tube 10 is installed in the connector-side corrugated tube connection member 20 in a predetermined state. Specifically, as shown in FIG. 10C, the distal end face of the corrugated tube 10 reaches the base 21c of the mesh-tube installation hole 21b or is close thereto. At this time, the contact faces 32a of the plurality of second spring portions 32 are electrically connected to the mesh-tube 12, namely, the electrical connection portion 14. Also, the urging force of the plurality of second spring portions 32 holds the end portion of the corrugated tube 10 to be concentric with respect to the mesh-tube installation hole 21b, and a uniform adhesive layer is formed between the inner face of the mesh-tube installation hole 21b and the outer face of the mesh-tube 12.

As indicated by an arrow Y10C in the figure, if the adhesive 19 flows in a direction of the contact faces 32a, since the contact faces 32a are pressing the outer surface of the mesh-tube 12, the adhesive 19 is prevented from entering the space between the contact faces 32a and the mesh-tube 12.

Thereafter, the operator fixes the operation portion side corrugated tube connection member, not shown, to the end portion of the corrugated tube 10 with which the connector-side corrugated tube connection member 20 has not been connected, to finish assembling the universal cable 4.

It should be noted that since the procedure for fixing the operation portion side corrugated tube connection member to the corrugated tube 10 is similar to the above-described procedure for fixing the connector-side corrugated tube connection member 20 to the end portion of the corrugated tube 10, a description thereof is omitted.

In this manner, the contact faces 32a of the plurality of second spring portions 32 are configured to press the outer surface of the mesh-tube 12 with a predetermined pressing force. As a result, the electrical connection portion 14 on which an adhesive is applied beforehand and the connector-side corrugated tube connection member 20 can be electrically connected to each other reliably through the conductive elastic member 30, and the corrugated tube 10 can be adhesively secured to the connector-side corrugated tube connection member 20.

Also, the end portion of the corrugated tube 10, which is the electrical connection portion 14, is pressed with the defined pressing force by the plurality of second spring portions 32, which are circumferentially provided at the predetermined substantially regular intervals. As a result, since the end portion of the corrugated tube 10 is concentric with respect to the mesh-tube installation hole 21b, a uniform adhesive layer is formed between the inner face of the mesh-tube installation hole 21b and the outer face of the mesh-tube 12, and thereby a fine adhesively secured state can be achieved. In addition, the center axis of the communicating hole 23 substantially matches with the center axis of the through hole 15 of the corrugated tube 10, thereby allowing for eliminating the inconvenience caused by the positional difference between the communicating hole 23 and the through hole 15.

In the foregoing embodiment, the conductive elastic member 30 including the first spring portion 31 and the second spring portions 32 has been provided in the circumferential concave portion 24. However, the conductive elastic member provided in the circumferential concave portion 24 is not limited to the conductive elastic member 30 and may be a ring-shaped conductive elastic member 30A shown in FIGS. 11A and 11B.

Figure 11A:
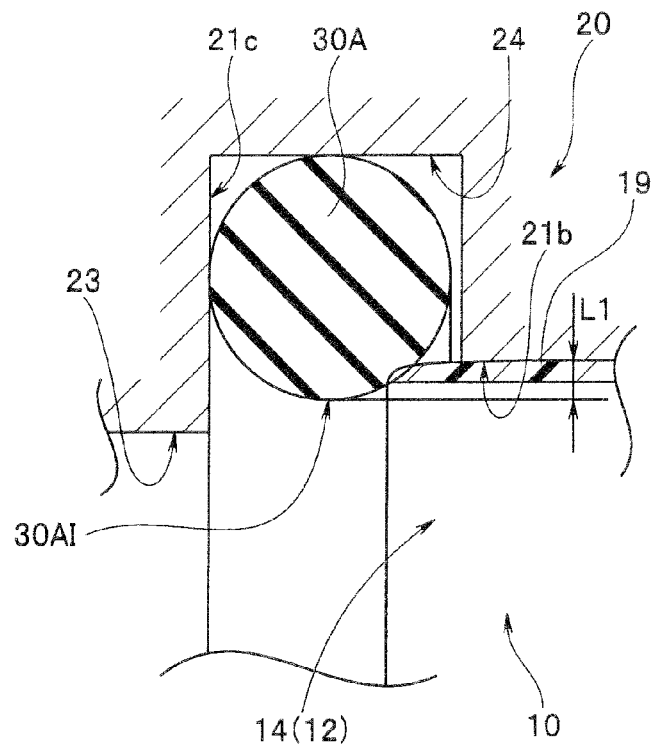
FIG. 11A is an example of another configuration of a conductive elastic member and is a diagram illustrating a ring-shaped conductive elastic member.
Figure 11B:
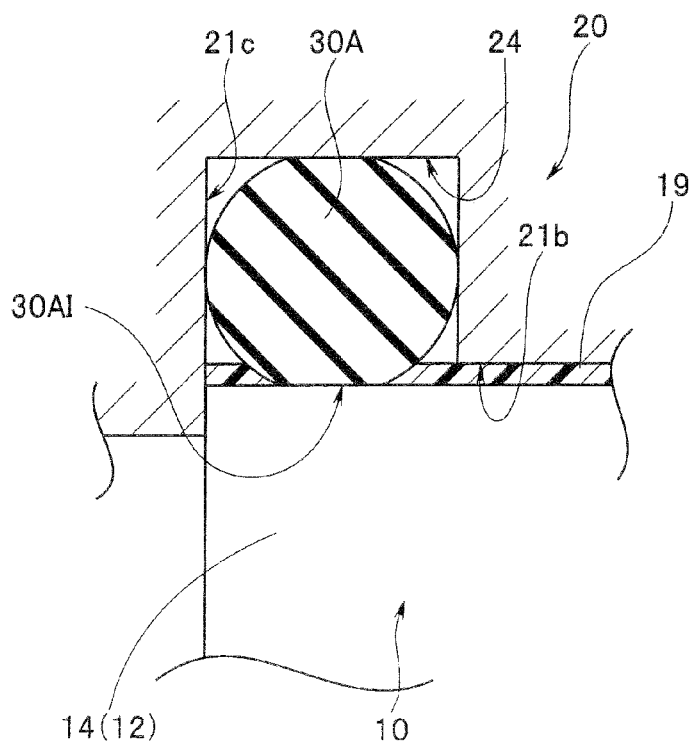
FIG. 11B is a diagram illustrating an action of the ring-shaped conductive elastic member.

The conductive elastic member 30A shown in FIGS. 11A and 11B is a conductive ring member having conductivity. The conductive elastic member 30A is elastically deformable radially and has an urging force for contacting the inner face of the circumferential concave portion 24 and the outer surface of the mesh-tube 12 with a predetermined pressing force.

The conductive elastic member 30A is installed in the circumferential concave portion 24. In the installation state, an inner circumferential face 30AI of the conductive elastic member 30A protrudes from the inner face of the mesh-tube installation hole 21b to the center axis direction of the connector-side corrugated tube connection member 20 by a predetermined dimension L1 as shown in FIG. 11A.

In this manner, by installing the ring-shaped conductive elastic member 30A in the circumferential concave portion 24, the inner circumferential face 30AI of the conductive elastic member 30A can evenly press the outer circumferential face of the electrical connection portion 14 to provide fine electrical connection and adhesive securing.

Figure 12:
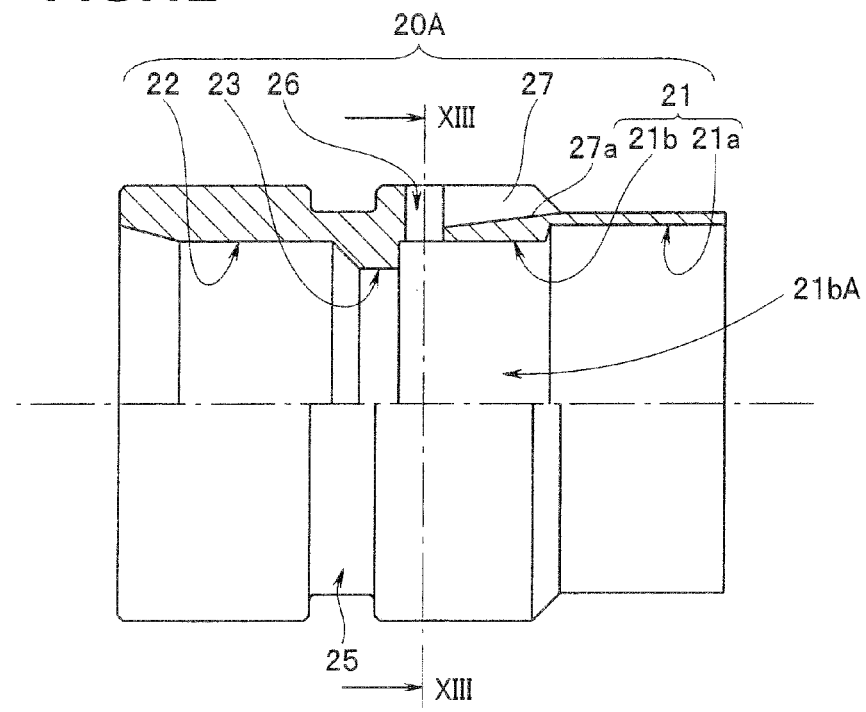
FIG. 12 is a diagram illustrating a connector-side corrugated tube connection member including through holes as conductive member installation portions in place of a circumferential concave portion.
Figure 13:
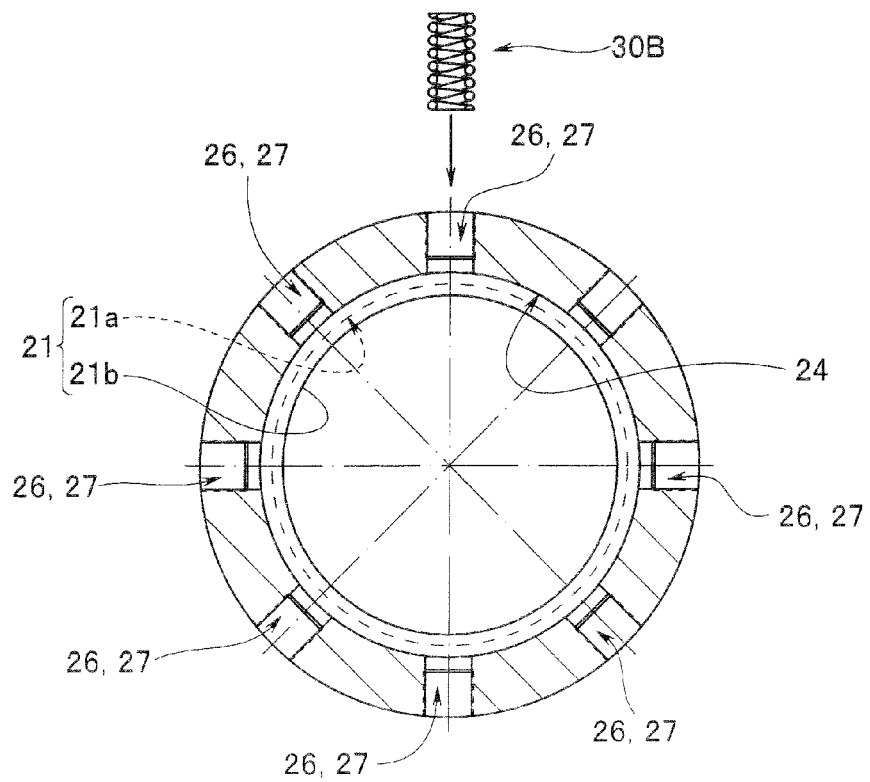
FIG. 13 is a cross-sectional view taken along a line XIII-XIII in FIG. 12.

In the foregoing embodiment, a conductive member installation portion is the circumferential concave portion 24. However, the conductive member installation portion is not limited to the circumferential concave portion 24. As shown in FIGS. 12 and 13, a through hole 26 that communicates outside of a connector-side corrugated tube connection member 20A with an internal space 21bA of the mesh-tube installation hole 21b may be a conductive member installation portion. A center axis of the through hole 26 is orthogonal to a center axis of the connector-side corrugated tube connection member 20A. The plurality of through holes 26 are circumferentially provided in the connector-side corrugated tube connection member 20A at predetermined intervals, for example, at 45 degrees intervals.

In the configuration in which conductive member installation portions are the through holes 26, conductive elastic members are conductive spring members, each of which is installed in each through hole. Specifically, the conductive spring members are coil springs 30B. Each of the coil springs 30B has an urging force for abutting the outer surface of the mesh-tube 12 with a predetermined pressing force. An outside diameter dimension of the coil springs 30B is configured to be smaller than an inside diameter dimension of the through hole 26 by a predetermined dimension. Thereby, the coil springs 30B are prevented from moving in a longitudinal axis direction of the connector-side corrugated tube connection member 20A.

Figure 14:
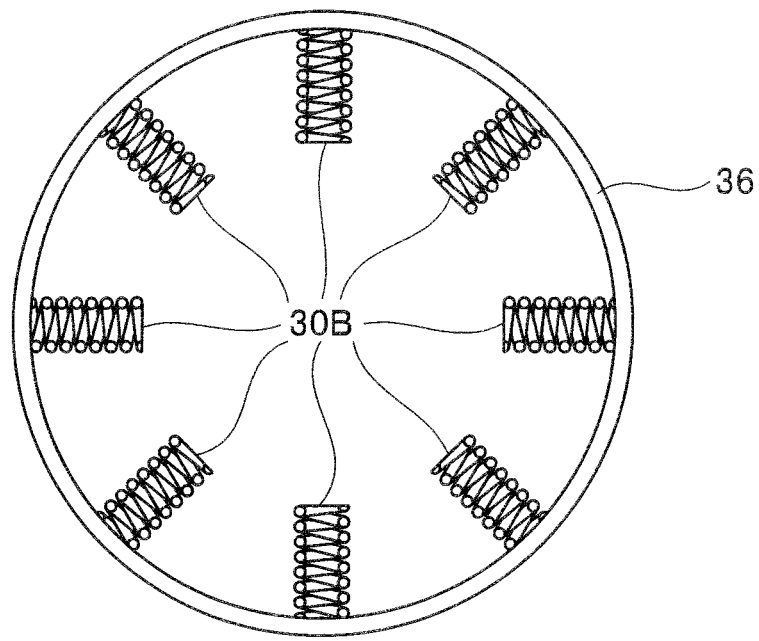
FIG. 14 is a diagram illustrating a conductive ring member in which a plurality of coil springs are arranged at equal intervals.

As shown in FIG. 14, the plurality of coil springs 30B are electrically connected, for example, by soldering, with an inner circumferential face of a conductive ring member 36 having conductivity and secured thereto in one piece. The conductive ring member 36 is installed on an outer circumference of the connector-side corrugated tube connection member 20A. An inside diameter of the conductive ring member 36 is configured to be electrically connected and secured to an outer surface of the connector-side corrugated tube connection member 20A by press-fitting or soldering.

The connector-side corrugated tube connection member 20A of the present embodiment includes, as shown in FIG. 12, spring guide grooves 27 at an outer surface of a side of the mesh-tube installation hole 21b. The spring guide grooves 27 are formed to lead the coil springs 30B compressed against an urging force into the through holes 26. Reference numeral 27a denotes a base and an inclined plane that lowers as it approaches the through holes 26. Thus, as the coil springs 30B move the base 27a toward the through holes 26, the coil springs 30B are gradually expands from the compressed state.

The plurality of coil springs 30B secured on the conductive ring member 36 are installed in the through holes 26 by following the procedure below.

Figure 15A:
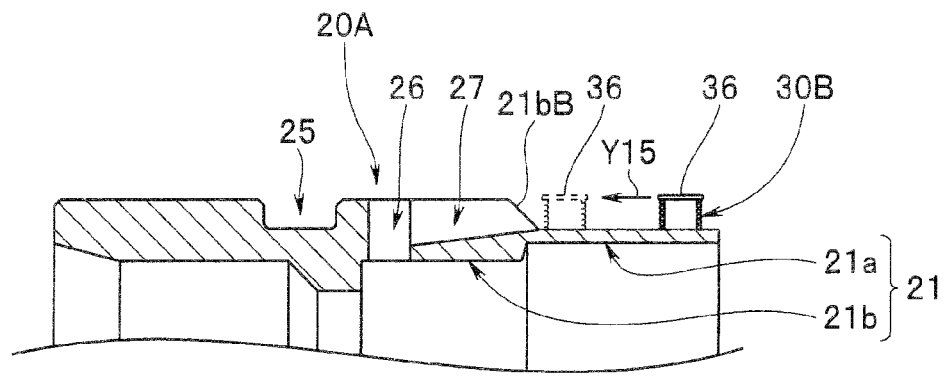
FIG. 15A is a diagram illustrating a procedure for installing the coil springs of the conductive ring member in through holes.

First, the operator compresses the plurality of coil springs 30B of the conductive ring member 36 as shown in FIG. 15A and installs the coil springs 30B on an outer surface of a side of the cover installation hole 21a of the connector-side corrugated tube connection member 20A.

Next, in order to move the coil springs 30B toward the through holes 26, the operator moves the conductive ring member 36 along the axis direction against the urging force of the coil springs 30B as indicated by an arrow Y15.

When the conductive ring member 36 comes close to a step portion 21bB near an outer surface at a side of the mesh-tube installation hole 21b as indicated by dashed lines in the figure, the operator positions each of the coil springs 30B at each of the spring guide grooves 27.

After positioning, the operator moves the conductive ring member 36 along the axis direction again. As a result, the conductive ring member 36 moves with the coil springs 30B installed in the spring guide grooves 27. When reaching the through holes 26, the coil springs 30B return to their natural length from the compressed state.

Figure 15B:
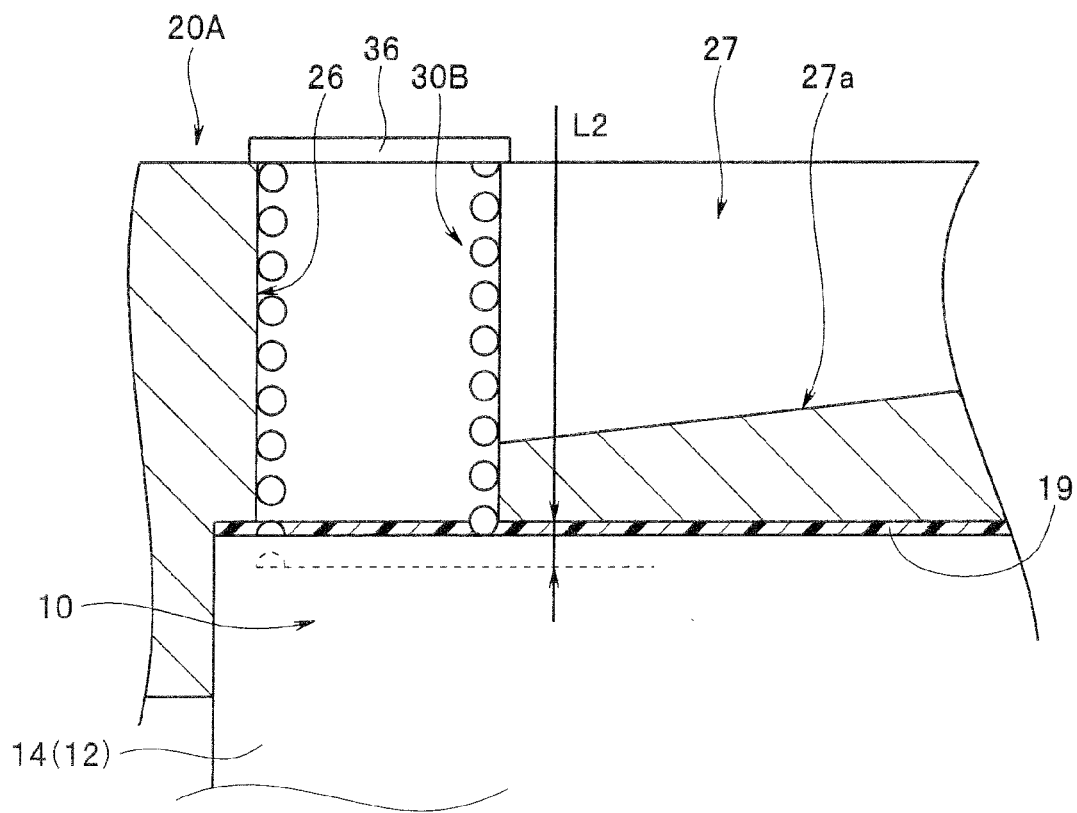
FIG. 15B is a diagram illustrating a state in which the coil springs of the conductive ring member are installed in the through holes.

That is, as shown in FIG. 15B, the coil springs 30B are installed in the through holes 26. In this state, the conductive ring member 36 is secured in one piece to the connector-side corrugated tube connection member 20A, for example, by soldering.

In this installation state, as indicated by a dashed line, distal end faces of the coil springs 30B protrude from the inner face of the mesh-tube installation hole 21b in the center axis direction of the connector-side corrugated tube connection member 20A by a predetermined dimension L2 as shown in FIG. 15B.

In this manner, the plurality of through holes 26 are provided in the connector-side corrugated tube connection member 20A, and the coil springs 30B fixed to the conductive ring member 36 are installed in the through holes 26. As a result, the distal end faces of the coil springs 30B being conductive elastic members press the outer circumferential face of the electrical connection portion 14, and thereby the same action and effect as those of the foregoing embodiment can be achieved.

To the connector-side corrugated tube connection members 20 and 20A of the universal cable 4 configured as described above, a conductive, for example, metal connector connecting member, not shown, is connected by screwing or the like. The connector connecting member is connected and secured by screwing or the like to a conductive, for example, metal connector body, not shown, configuring the connector 4a.

On the other hand, to the operation portion side corrugated tube connection member not shown, a conductive, for example, metal operation portion connecting member, not shown, is connected by screwing or the like. The operation portion connecting member is connected and secured by screwing or the like to a conductive, for example, metal body frame, not shown, configuring the operation portion 3.

Thereby, the body frame of the operation portion 3, the conductive tube member composed of the mesh-tube 12 and the helical tube 13 of the universal cable 4, and the connector body of the connector 4a are electrically connected to each other. Also, in the flexible tube portion 5, the body frame of the operation portion 3, the conductive tube member composed of the mesh-tube and the helical tube of the flexible tube portion 5, and the bending portion 6 are electrically connected to each other.

Thus, in the electronic endoscope 1 with the connector 4a connected to a video processor, for example, a conductive distal end portion body configuring the distal end portion 7, a conductive bending piece configuring the bending portion 6, the conductive tube member composed of the mesh-tube and the helical tube of the flexible tube portion 5, the body frame of the operation portion 3, the conductive tube member composed of the mesh-tube 12 and the helical tube 13 of the universal cable 4, the connector body of the connector 4a, and the video processor are electrically connected to each other. As a result, a radiation noise radiated from a signal cable inserted in the insertion portion 2, the operation portion 3, and the universal cable 4 can be reduced to a ground level.

Conventionally, in a signal cable installed in the operation portion 3, an electromagnetic wave shielded wire covered by the sheath is peeled off the signal cable, and the peeled-off shielded wire is fixed to the body frame of the operation portion 3 and grounded.

However, since the shielded wire is thin, when being fixed and grounded, the shielded wire might be damaged, for example, cut, scraped, and deformed to be thinner. Also, because an area of the grounded shielded wire is small as compared with the body frame, it has been difficult to obtain a sufficient grounding effect.

Figure 16:
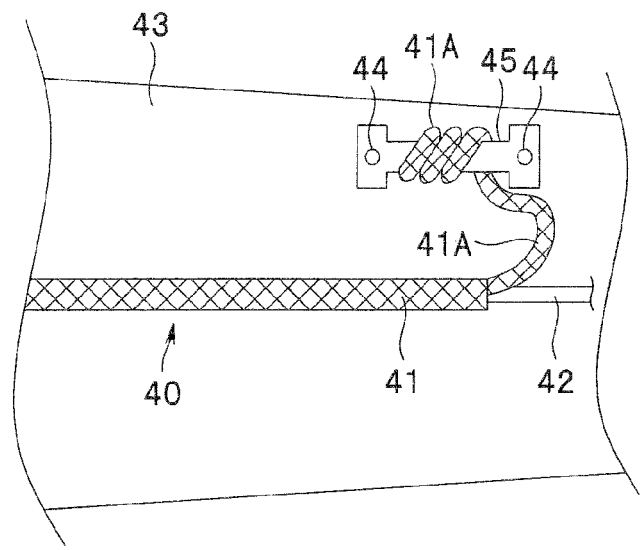
FIG. 16 is a diagram illustrating a state in which a grounding plate member is secured to a body frame using screws with a shielded wire of a signal cable being wound around the grounding plate member.
Figure 17:
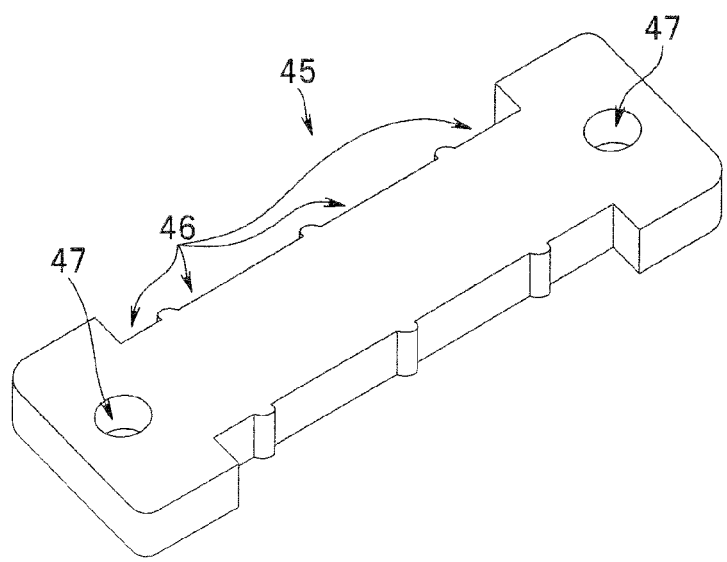
FIG. 17 is a diagram illustrating the grounding plate member.

In the present embodiment, as shown in FIG. 16, in a signal cable 40, an electromagnetic wave shielded wire 41 covered by the sheath is peeled off a conductor 42 in the signal cable 40. A peeled-off shielded wire 41A is wound around a grounding plate member 45 shown in FIG. 17. Then, the grounding plate member 45 is fixed on a body frame 43 of the operation portion with screws 44 and grounded.

The grounding plate member 45 is a conductive metal plate. The grounding plate member 45 is provided with a plurality of grooves for shielded wire 46 for winding the shielded wire 41A and with screw holes 47 in which the screws 44 are inserted.

In this manner, winding a shielded wire of a signal cable around a grounding plate member can increase an area of a contact face as well as screwing the grounding plate member around which the shielded wire is wound with a body frame can provide firm fixing without damaging the shielded wire.

Also, a flexible printed circuit (hereinafter, abbreviated as FPC) 55 is used for connecting circuit boards in the operation portion to each other. Conventionally, in order to attenuate electromagnetic waves generated from the FPC 55, the FPC 55 has been passed through a through hole 50a of a magnetic body 50, called ferrite core.

However, since a magnetic body has large mass, for example, an impact on an operation portion from outside may cause magnetic body failure or an impact load may move the magnetic body to cause the FPC to also move, thereby disconnecting the circuit board of the FPC from a connection portion.

Figure 18:
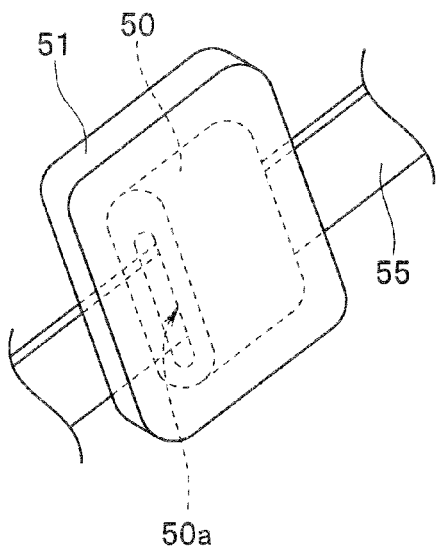
FIG. 18 is a diagram illustrating a state in which a magnetic body having a through hole in which a flexible printed circuit is inserted is wrapped by an elastic body.
Figure 19:
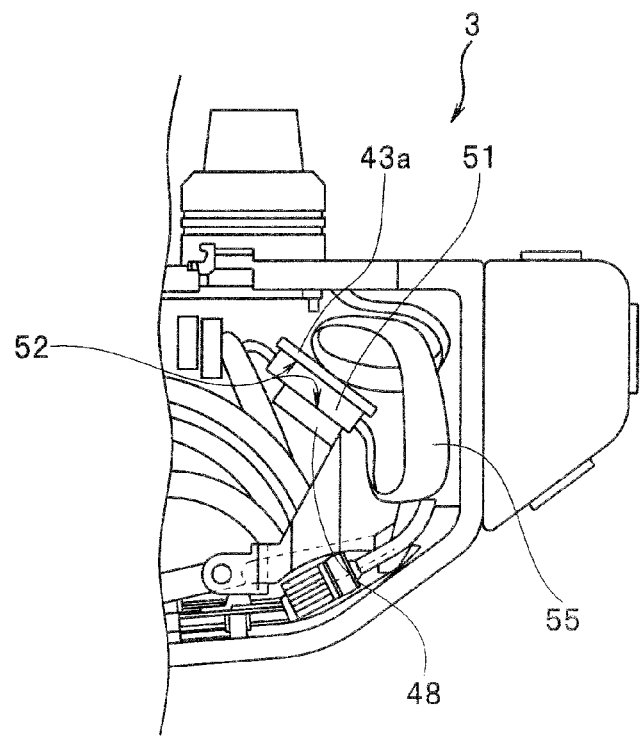
FIG. 19 is a diagram illustrating a state in which the magnetic body wrapped by the elastic body is held and fixed in a magnetic body disposition gap provided in the body frame.

In the present embodiment, as shown in FIG. 18, the magnetic body 50 is wrapped by an elastic body 51. On the other hand, as shown in FIG. 19, a magnetic body disposition gap 52 is provided in the operation portion 3. The magnetic body disposition gap 52 is composed of a part 43a of the body frame 43, a holding plate 48 mounted on the body frame 43, and the like. A width dimension of the magnetic body disposition gap 52 is configured to be smaller than a width dimension of the elastic body 51 which has wrapped the magnetic body 50, by a predetermined dimension.

Then, the magnetic body 50 wrapped by the elastic body 51 is inserted and installed between the part 43a of the body frame 43 and the holding plate 48. As a result, the elastic body 51 wrapping the magnetic body 50 is held and fixed in the magnetic body disposition gap 52.

According to this configuration, without increasing the number of components such as brackets or cable ties and securing a magnetic body in an operation portion with a bracket or a cable tie, the magnetic body can be protected against an impact and the magnetic body can be easily and reliably prevented from being moved by an impact load.

Now, a configuration of the distal end portion 7 of the electronic endoscope 1 will be described.

Figure 20:
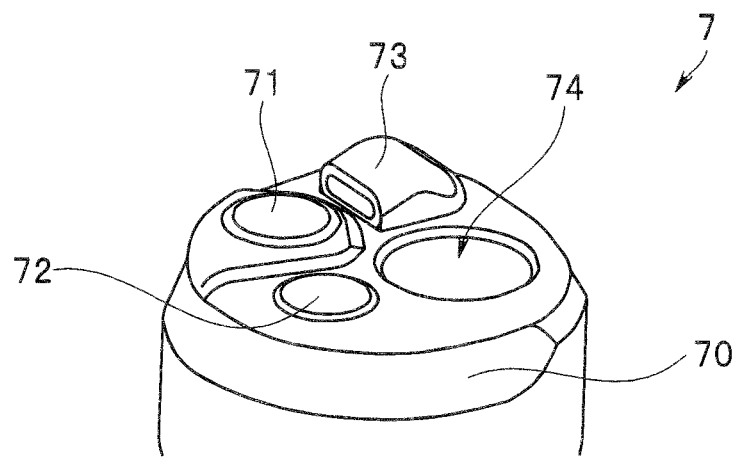
FIG. 20 is a diagram illustrating a distal end face of a distal end portion body configuring a distal end portion.

As shown in FIG. 20, the distal end portion 7 includes a distal end portion body 70. An observation lens 71, an illumination lens 72, and a nozzle 73 are provided on a distal end face of the body 70. Reference numeral 74 denotes a channel opening.

Generally, a nozzle is formed by bending a pipe-shaped member. The bent nozzle is disposed in a nozzle installation opening formed in a distal end portion body.

For example, Japanese Patent Application Laid-Open Publication No. 2001-258825 (hereinafter, referred to as the document) discloses an endoscope including a fluid jet nozzle. The fluid jet nozzle is composed of, as shown in FIGS. 9, 10, and 11 in the document, a nozzle body and a nozzle supporting member formed in one piece around a bent-shaped portion of the nozzle body.

Then, the fluid jet nozzle is disposed in an opening concave portion provided in the distal end portion of the distal end portion body. According to this configuration, the nozzle supporting member prevents an unnecessary space from being formed in the distal end portion body.

However, as shown in FIG. 10 in the document, since the nozzle supporting member has a cross-sectional shape of a substantial bullet, the cross section is larger than a diameter dimension of a pipe part. For this reason, it has been challenging to reduce the diameter of the insertion portion.

Figure 21:
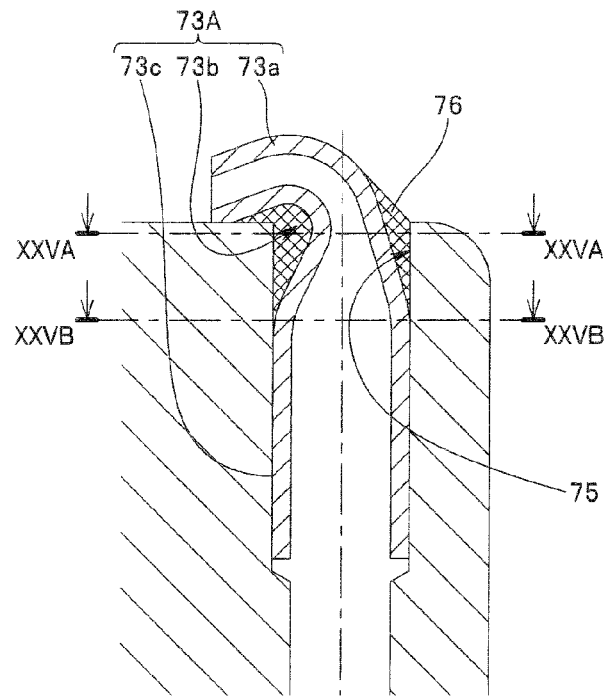
FIG. 21 is a diagram illustrating a nozzle disposed in the distal end portion body.
Figure 22:
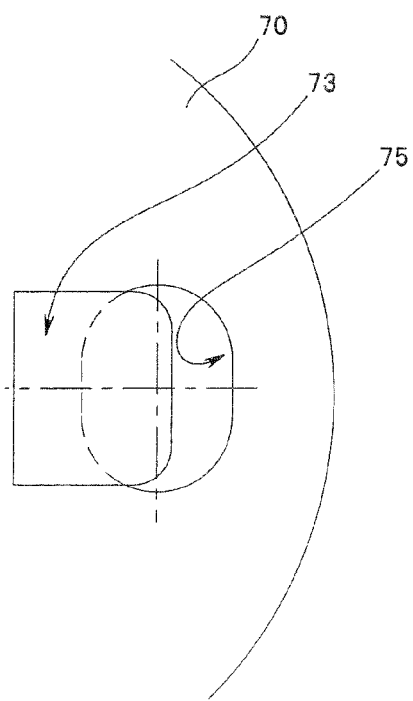
FIG. 22 is a diagram illustrating the nozzle and a nozzle installation bore of the distal end face as viewed from the front.

A nozzle 73A shown in FIG. 21 is obtained by bending a pipe member. The nozzle 73A includes a nozzle portion 73a, a bent-shaped portion 73b, and a pipe portion 73c. On the other hand, a nozzle installation opening 75 has an oval shape as shown in FIG. 22.

Figure 23:
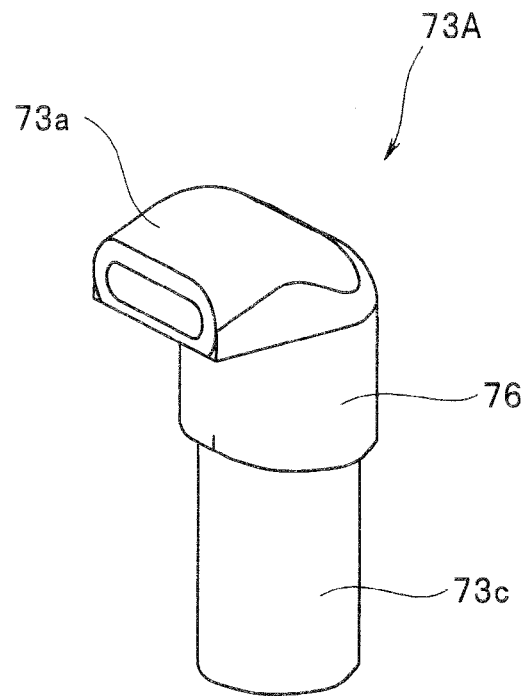
FIG. 23 is a perspective view showing a nozzle in which a nozzle supporting member is formed in one piece around a bent-shaped portion.
Figure 24:
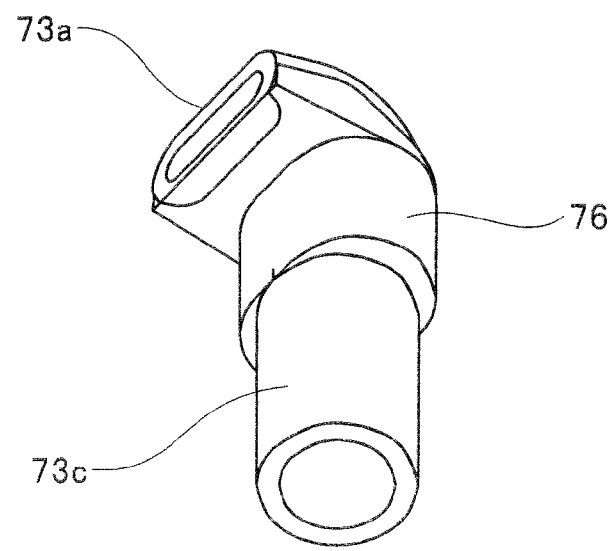
FIG. 24 is a perspective view for comparison between a shape of the nozzle supporting member and a shape of the pipe portion.

Then, as shown in FIGS. 21, 23, and 24, in the nozzle 73A installed in the nozzle installation opening 75, a nozzle supporting member 76 having a cross-sectional outside shape of an oval is formed around the bent-shaped portion 73b in one piece. In consideration of installation into the nozzle installation opening 75, the nozzle supporting member 76 is smaller than the nozzle installation opening 75 by a predetermined dimension.

Figure 25A:
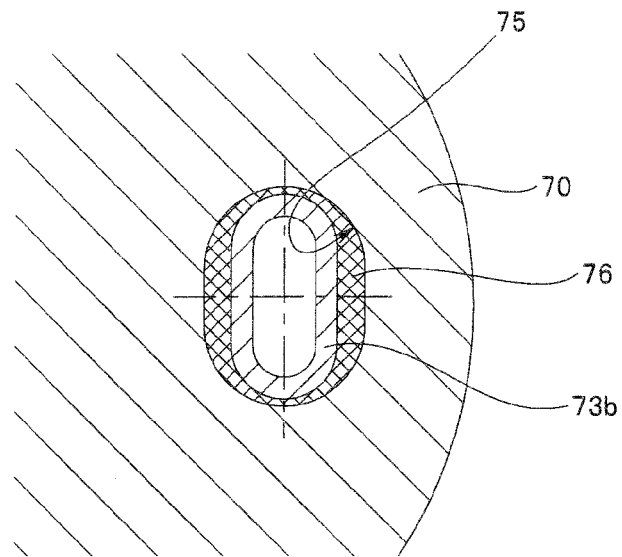
FIG. 25A is a cross-sectional view taken along a line XXVA-XXVA in FIG. 21.
Figure 25B:
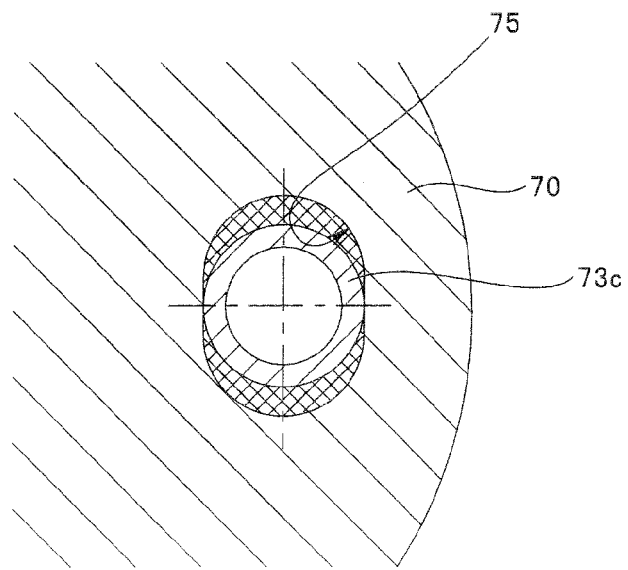
FIG. 25B is a cross-sectional view taken along a line XXVB-XXVB in FIG. 21.

In this manner, the nozzle supporting member 76 having a cross-sectional outside shape of an oval is provided around the bent-shaped portion 73b, and thereby an unnecessary space can be reliably prevented from being formed in the distal end portion body 70 as shown in FIGS. 25A and 25B.

On the other hand, a through hole for illumination optical system for configuring an illumination optical system is provided in the distal end portion body. In the through hole for illumination optical system, an illumination lens and a light guide mouth ring in which a light guide fiber bundle is inserted and installed are adhesively secured.

Figure 26:
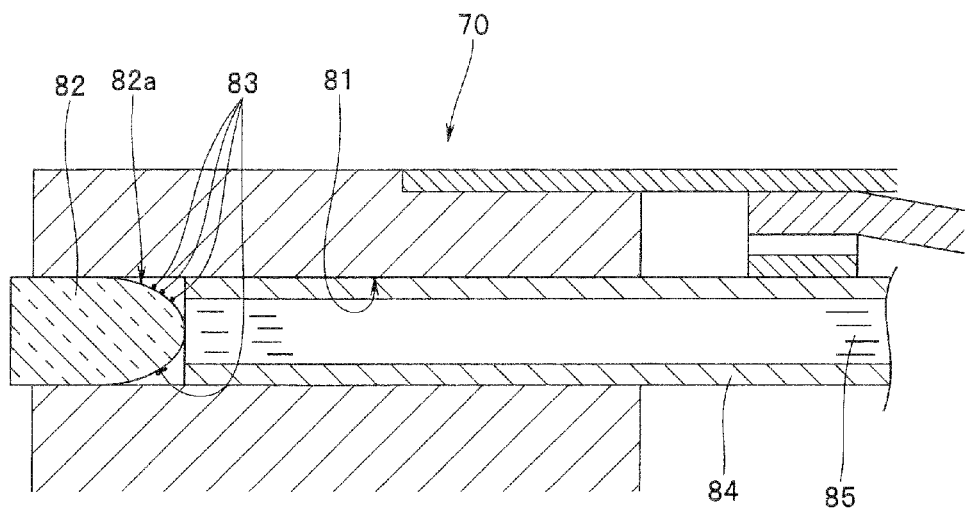
FIG. 26 is a diagram illustrating a distal end portion body provided with a straight-shaped through hole for illumination optical system.

As shown in FIG. 26, if a through hole 81 for illumination optical system, the hole being formed in the distal end portion body 70, is straight, and an illumination lens 82 is inserted to a distal end side (left side on the figure) of the through hole 81 for illumination optical system so as to be adhesively secured, when the illumination lens 82 is inserted in the through hole 81 for illumination optical system, an adhesive 83 applied to an outer circumferential face of the illumination lens 82 may run off to a side of a light guide mouth ring 84 and be attached to a lens surface 82a.

If the adhesive 83 is attached to the lens surface 82a, inconveniences occur, for example, an amount of illuminating light is reduced or a part of illuminating light falls. Reference numeral 85 denotes a light guide fiber bundle.

Figure 27:
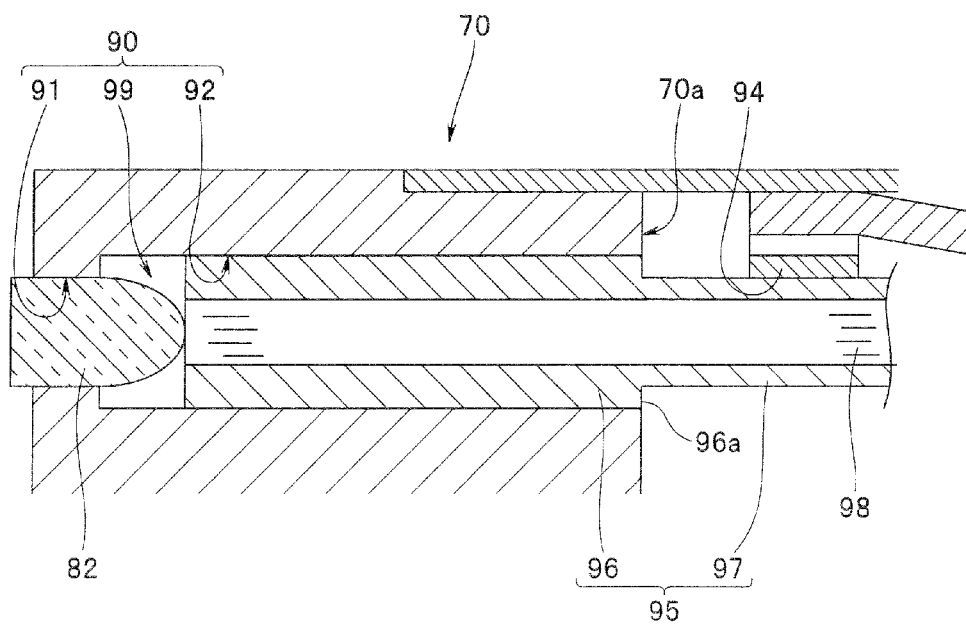
FIG. 27 is a diagram illustrating a distal end portion body provided with a straight-shaped through hole for illumination optical system.

In an illumination optical system of the electronic endoscope 1 of the present application, in order to prevent an adhesive from running off to a side of a light guide mouth ring and being attached to a lens surface, a through hole 90 for illumination optical system has a stepped shape as shown in FIG. 27.

As shown in FIG. 27, the distal end portion body 70 is provided with the stepped through hole 90 for illumination optical system, the hole being composed of a thin bore 91 and a thick bore 92. The thin bore 91 is an illumination lens installation bore, and the thick bore 92 is a mouth ring installation bore in which a light guide mouth ring 95 is installed.

In the present embodiment, the light guide mouth ring 95 includes a thick diameter portion 96 and a thin diameter portion 97. The thick diameter portion 96 is installed in the thick bore 92. A length of the thick diameter portion 96 from a distal end face to a proximal end face is configured so that if a proximal end face 96a of the thick diameter portion 96 matches with a proximal end face 70a of the distal end portion body 70 in surface, a light guide fiber bundle 98 in the light guide mouth ring 95 abuts a proximal end of the illumination lens 82.

In the installation configuration, the thin diameter portion 97 projects from the proximal end face 70a of the distal end portion body 70. An outside diameter dimension of the thin diameter portion 97 is defined to a dimension that prevents interference with contents such as a string guide 94.

In this manner, the light guide mouth ring 95 is composed of the thick diameter portion 96 installed in the thick bore 92 and the thin diameter portion 97 protruding from the proximal end face 70a of the distal end portion body 70, and thereby a space 99 for adhesive reservoir capable of being an adhesive relief portion can be provided at a proximal end side of the illumination lens installation bore.

According to this configuration, when there arises an excess adhesive for fixing the illumination lens 82 to the illumination lens installation bore, the excess adhesive goes out along a wall configuring a distal end side of the thick bore 92 configuring the space 99 for adhesive reservoir, without running off from the proximal end side of the illumination lens installation bore onto the lens surface 82a.

Further, since the outside diameter dimension of the thin diameter portion 97 of the light guide mouth ring 95, the thin diameter portion 97 being exposed from the proximal end face 70a of the distal end portion body 70, is regulated, the light guide mouth ring 95 can be reliably prevented from interfering with contents such as the string guide 94.

Furthermore, the light guide fiber bundle 98 in the light guide mouth ring 95 is configured to abut the illumination lens 82 when the proximal end face 96a of the thick diameter portion 96 matches with the proximal end face 70a of the distal end portion body 70 in surface. Therefore, it can be recognized that an insertion position of the light guide mouth ring 95 is approaching the position of the illumination lens 82 by visually observing a position of the proximal end face 96a of the thick diameter portion 96 which is being inserted in the thick bore 92.

It should be noted that the present invention is not limited to the aforementioned embodiments, and a variety of modifications can be made within the range without departing from the gist of the present invention.

What is claimed is:

1. An electronic endoscope comprising:
   a flexible tube portion configuring an insertion portion extending from an operation portion; and
   a universal cable extending from a side of the operation portion,
   wherein the flexible tube portion and the universal cable each comprises a laminated tube member comprising:
      a conductive tube member; and
      an insulating cover covering the conductive tube member;
   wherein the electronic endoscope further comprises:
      a conductive corrugated tube connection member having a fixing hole, the fixing hole including a first installation hole in which the insulating cover of the laminated tube member is installed, and a second installation hole in which the conductive tube member, as an electrical connection portion, exposed by peeling the insulating cover is installed, wherein the laminated tube member inserted in the fixing hole is secured with an adhesive; and
      a conductive elastic member that is elastically deformable radially, electrically connects the electrical connection portion inserted in the second installation hole of the corrugated tube connection member to the corrugated tube connection member, and is configured to have an urging force for contacting an outer surface of the conductive tube member as the electrical connection portion with a predetermined pressing force and remove an adhesive applied on the electrical connection portion with the pressing force.

2. The electronic endoscope according to claim 1, wherein the pressing force of the conductive elastic member is substantially uniform on the outer surface of the electrical connection portion.

3. The electronic endoscope according to claim 1, wherein the conductive elastic member comprises:
   a first spring portion that is C-shaped and elastically deformable radially, and installed in a circumferential concave portion provided in the second installation hole included in the corrugated tube connection member and formed as a circumferential groove of a predetermined depth dimension from an inner face of the second installation hole by the elastic force to be electrically connected to the corrugated tube connection member, and
   a plurality of second spring portions that are provided on the first spring portion at predetermined intervals, and caused, by an urging force toward a center axis direction of the conductive tube member, to contact and be electrically connected with the outer surface of the conductive tube member.

4. The electronic endoscope according to claim 1, wherein the conductive elastic member is a conductive ring member which is installed in a circumferential concave portion provided in the second installation hole and formed as a circumferential groove of a predetermined depth dimension from an inner face of the second installation hole and elastically deformable radially, and which contacts an inner face of the fixing hole and the outer surface of the conductive tube member.

5. The electronic endoscope according to claim 1, wherein the conductive elastic member is conductive spring members electrically connected and secured to a conductive ring member installed on an outer circumferential face of the corrugated tube connection member, and installed in a plurality of through holes that communicate outside of the corrugated tube connection member with an internal space of the second installation hole and are circumferentially provided in the corrugated tube connection member at predetermined intervals, to contact the outer surface of the conductive tube member.

* * * * *